(12) United States Patent
Simonetti

(10) Patent No.: US 6,295,465 B1
(45) Date of Patent: Sep. 25, 2001

(54) MYOCARDIAL PERFUSION STUDIES USING MAGNETIC RESONANCE IMAGING

(75) Inventor: Orlando P. Simonetti, Naperville, IL (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/251,550

(22) Filed: Feb. 17, 1999

(51) Int. Cl.[7] .................................................... A61B 5/055
(52) U.S. Cl. ............................................. 600/413; 600/420
(58) Field of Search ..................................... 600/413, 419, 600/420; 324/306, 309

(56) References Cited

U.S. PATENT DOCUMENTS

| | | | |
|---|---|---|---|
| 5,245,282 | * | 9/1993 | Mugler, III et al. . |
| 5,320,099 | * | 6/1994 | Roberts et al. . |
| 5,357,959 | * | 10/1994 | Fishman . |
| 5,402,785 | * | 4/1995 | Leigh et al. . |
| 5,685,305 | * | 11/1997 | Moonen et al. . |
| 5,692,508 | * | 12/1997 | Simonetti et al. . |
| 5,713,358 | * | 2/1998 | Mistretta et al. . |
| 5,830,143 | * | 11/1998 | Mistretta et al. . |
| 5,908,386 | * | 6/1999 | Ugurbil et al. ........................ 600/410 |
| 5,924,987 | * | 7/1999 | Meaney et al. . |
| 6,121,775 | * | 9/2000 | Pearlman ............................. 324/309 |
| 6,192,264 | * | 2/2001 | Foo et al. ............................. 600/413 |

FOREIGN PATENT DOCUMENTS

WO 99/06849   2/1999   (WO) .

OTHER PUBLICATIONS

XP-002083542, Edelman, "Contrast–enhanced echo–planar MR imaging of myocardial perfusion . . . " Mar. 1, 1994, pp. 771–777.

XP002122932, Prince, "Breath–Held 3D Gadolinium–Enhanced Renal Artery MRA" 1995, p. 539.

XP0000885245, Schwitter, "Normal Myocardial Perfusion Assesed with Mulitshot Echo–Planar Imaging" Jan. 1997, pp. 140–147.

* cited by examiner

Primary Examiner—Marvin M. Lateef
Assistant Examiner—Shawna J Shaw
(74) Attorney, Agent, or Firm—Mark H. Jay

(57) ABSTRACT

Gadolinium-based MR contrast agent is administered to a patient. Acquisition of MR data begins at the latest when the bolus of MR contrast agent reaches the patient's heart and continues throughout the first-pass of contrast agent through the coronary circulation. Advantageously, the acquisition is carried out using a T1-weighted, three-dimensional gradient echo sequence that is synchronized to the patient's cardiac cycle to acquire MR data only during diastole, and a T1-weighting magnetization preparation such as inversion-recovery or saturation-recovery is used.

11 Claims, 2 Drawing Sheets

MYOCARDIAL PERFUSION STUDIES USING MAGNETIC RESONANCE IMAGING

BACKGROUND OF THE INVENTION

The invention relates to cardiology, and more specifically relates to myocardial perfusion studies carried out using magnetic resonance (MR) imaging.

Cardiologists use myocardial perfusion studies for the noninvasive diagnosis of coronary artery disease ("CAD"). In a conventional myocardial perfusion study, the patient is injected with a radioisotope tracer (e.g. $^{201}$Tl or $^{99m}$Tc) and a scintillation camera is used to form a three-dimensional image of the tracer distribution within the patient's heart. (This imaging technology is known as "nuclear medicine".) This image permits a diagnostician to differentiate regions of the myocardium that receive normal blood flow (regions that are normally "perfused"), from those with abnormally reduced blood flow (caused by CAD). Monitoring myocardial perfusion under predetermined conditions (e.g. with the patient at rest and/or under exercise- or pharmacologically-induced stress) allows cardiologists to diagnose the existence and severity of CAD.

MR imaging is capable of spatial resolution that is an order of magnitude greater than nuclear medicine imaging, offering the possibility of greater sensitivity and specificity for the detection and delineation of regional myocardial perfusion defects. For this reason, doctors have long sought to carry out myocardial perfusion studies using the MR modality.

In such attempts, the patient's blood has been labeled using a T1-lowering contrast agent (such as Gd-DTPA), which makes the blood appear bright in a T1-weighted MR image. In this way, differences in regional myocardial perfusion can be identified by differences of signal intensity within the imaged myocardium. Normally perfused tissue will show signal enhancement with the arrival of T1-shortening contrast agent; poorly perfused tissue will show no enhancement or enhancement that is diminished and delayed.

Attempts to image myocardial perfusion using the MR modality have had limited success and have not yet been put into clinical practice. One reason for this has been that researchers have focussed upon quantification of myocardial bloodflow. To quantify myocardial bloodflow using first-pass enhancement techniques, the MR signal must be sampled rapidly enough to produce about one image per second. (Such a high temporal resolution is required to characterize the enhancement curve with accuracy sufficient to estimate myocardial bloodflow.)

Even with modern high-performance MR imagers, the price of achieving such high temporal resolution is a reduction in spatial resolution and signal-to-noise ratio, and a reduction in the volume that is imaged (such a volume reduction is known as a reduction in "coverage"). As a result, the quality of MR myocardial perfusion studies has been unacceptable for diagnostic purposes. So, too, it has been impossible to cover the entire heart in a single study, severely limiting the value of the technique as a means of noninvasively detecting CAD.

It would be advantageous to provide a method for carrying out a myocardial perfusion study using MR imaging, in which the reconstructed MR images had sufficiently good spatial resolution, sufficiently good signal-to-noise ratio, and sufficiently good contrast between normal and abnormal tissue as to be acceptable for diagnostic purposes, and in which the entire heart could be imaged in a single study.

One object of the invention is to provide a method for carrying out a myocardial perfusion study using MR imaging, in which the reconstructed MR images can have a high spatial resolution and a high signal-to-noise ratio.

Another object is to provide a method for carrying out a myocardial perfusion study using MR imaging, in which reconstructed MR images of the entire heart can be produced on the basis of a single study.

Another object is, in general, to improve on known methods of this general type.

The invention proceeds from the realization that an MR myocardial perfusion study need not have high temporal resolution in order to be diagnostically valuable. Rather, if acquisition of MR image data is accurately timed to take place throughout the several seconds it takes for a bolus of MR contrast agent to make its first pass through the heart, it is possible to produce MR myocardial perfusion images of high diagnostic value.

In accordance with the invention, a bolus of MR contrast agent is administered to the patient, and MR data acquisition occurs when that bolus makes its first pass through the heart. (Advantageously, the acquisition begins when or shortly before the bolus reaches the heart, and ends when or shortly after the bolus leaves the heart.) The acquisition is gated to the patient's cardiac cycle. In the preferred embodiment, lines of MR data are acquired only during the diastolic phase in successive cardiac cycles, and advantageously while the patient holds his or her breath. These measures minimize cardiac wall motion during MR data acquisition and thereby maximize the spatial resolution of the reconstructed MR images of the heart.

Advantageously, and in accordance with the preferred embodiment, the T1-weighting of the MR signal is emphasized. This can be accomplished by using magnetization preparation of the inversion-recovery or saturation-recovery types. This results in an especially advantageous reconstructed MR image, because the contrast agent is more prominently displayed in the MR image, making it easier to distinguish between perfused and unperfused myocardial regions.

In the preferred embodiment, MR data acquisition is carried out using an MR pulse sequence of the T1-weighted, three-dimensional, gradient-echo type. Three-dimensional pulse sequences make it possible to image the heart with contiguous thin sections. Gradient-echo pulse sequences make it possible to collect many lines of MR data in a short time span (because such sequences can have a very short repetition time TR).

As stated above, MR data are acquired while the bolus of the MR contrast agent is making its first pass through the heart, and it is therefore necessary to make sure that data acquisition occurs at the correct time. At this writing, the inventor believes there are two ways in which this can be efficiently accomplished. The first is to experimentally establish the time delay between the injection of the MR contrast agent and the arrival of the MR contrast agent at the left ventricle of the patient's heart. This delay can then be used to start three-dimensional data acquisition after injection of the MR contrast agent. In practice, this time delay can be measured by injecting the patient with a small dose of MR contrast agent and using a two-dimensional acquisition having a high temporal resolution to determine when the MR contrast agent has reached the left ventricle. The second is to acquire, reconstruct and display two-dimensional images in real time after the contrast agent has been injected, and to switch to a three-dimensional acquisition when the contrast agent reaches the left ventricle. As of this writing, the first method has been used; work on the second method is ongoing.

BRIEF DESCRIPTION OF THE DRAWINGS

The invention will be better understood with the aid of the illustrative and non-limiting drawings, in which.

DETAILED DESCRIPTION OF PREFERRED EMBODIMENTS

Figure 1:
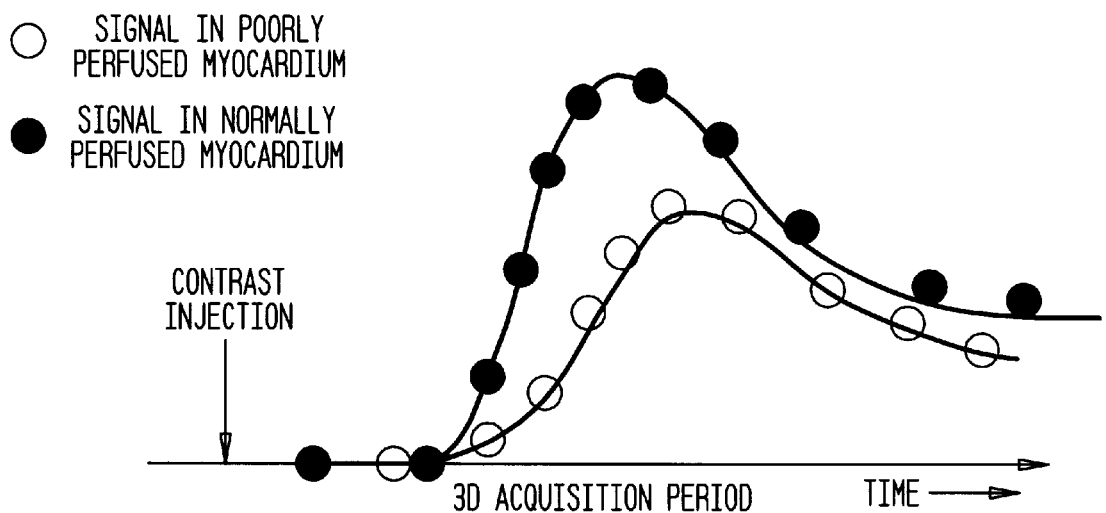
FIG. 1 schematically illustrates the relationships between the MR signals produced by normally- and poorly-perfused myocardial tissue after perfusion with blood labeled with Gd contrast agent.

Experiments have been conducted in which Gd-DTPA MR contrast agent has been administered to animals with surgically created myocardial perfusion defects and MR data of the entire heart acquired while the bolus of MR contrast agent is making its first pass through the heart. These experiments show that differences in perfusion of myocardial tissue produce differences in the MR signals produced by the myocardial tissue. More specifically, as is shown in FIG. 1, normally perfused myocardium enhances faster and more intensely than does poorly perfused myocardium. Hence, in accordance with the invention, the heart is imaged while the bolus of MR contrast agent is making its first pass through the patient's heart.

In accordance with the preferred embodiment of the invention, the T1-weighting of the MR signal is emphasized. This can be done using magnetization preparation of the inversion-recovery type or the saturation-recovery type. Regardless which type of magnetization preparation is used, the timing of MR data acquisition following magnetization preparation is chosen to suppress the signal from myocardium prior to the injection of contrast agent. This is accomplished based on the known T1 relaxation time of myocardium, and can if necessary be adjusted for individual differences in each patient.

Although inversion-recovery magnetization preparation produces reconstructed MR images having better contrast characteristics, it is less preferable when e.g. the patient suffers from arrythmia. For this reason and others, it is presently believed that saturation-recovery magnetization preparation may be preferable, but this has not been determined with certainty.

In accordance with the preferred embodiment, acquisition of lines of MR data is carried out while the patient is holding his or her breath, using an ECG-gated MR pulse sequence that acquires lines of MR data only during diastole. These measures minimize cardiac motion during acquisition of lines of MR data; breath-holding reduces motion caused by respiration, and cardiac motion during diastole is less than during systole.

In further accordance with the preferred embodiment, acquisition of lines of MR data is carried out using a T1-weighted, three-dimensional gradient-echo sequence. T1-weighting emphasizes the contribution of the MR contrast agent to the reconstructed image, and thereby improves the diagnostic quality of that image. A three-dimensional MR pulse sequence generates thin contiguous sections. A gradient-echo MR pulse sequence makes it possible to speed acquisition of MR data by using a short repetition time TR.

Figure 2:
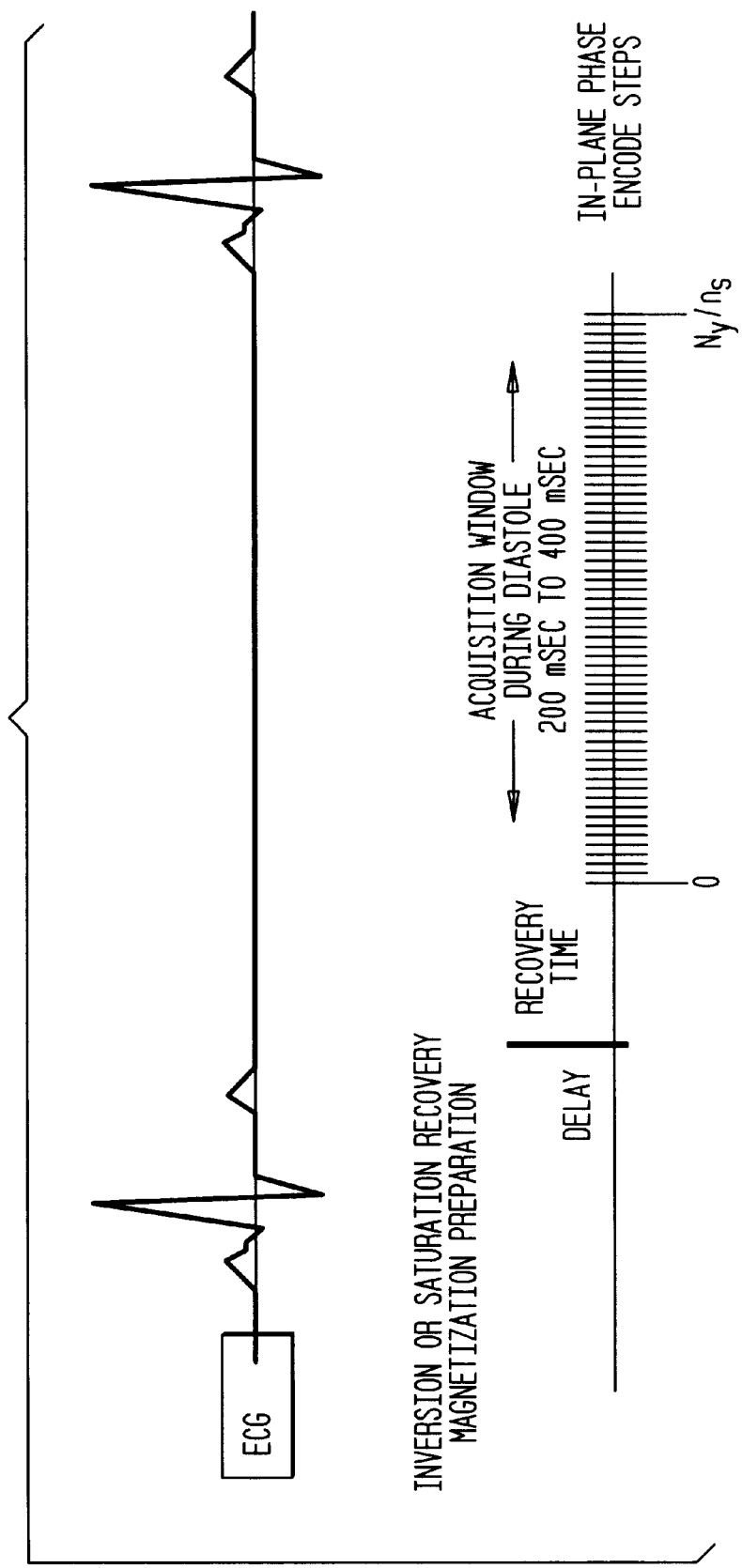
FIG. 2 is a diagram of an MR pulse sequence used in accordance with the preferred embodiment of the invention.

FIG. 2 illustrates a presently preferred MR pulse sequence that can be used in accordance with the invention. A typical study might have an in-plane matrix size of 126 by 256 and might acquire eight slice partitions (interpolated to sixteen), with sixty-three lines per cardiac cycle at a repetition time TR of four msec (for a total of 252 msec acquisition during each cardiac cycle). Using such parameters, sixty-three lines of MR data would be acquired during each cardiac cycle, and it would take sixteen cardiac cycles to fill up eight matrices of 126 lines and to thereby acquire sufficient data to reconstruct all eight slice partitions. (Most patients can easily hold their breaths for sixteen cardiac cycles.) In each cardiac cycle, the R-wave trigger signal initiates the application of a magnetization preparation pulse, followed by a delay time specified to maximize T1 contrast in the image and to position the data acquisition so that it occurs in the diastolic phase in each heartbeat.

Typical values for the repetition time TR can advantageously be 2.5 msec to 4.0 msec. Typically, there may be one to four segments, and there may be 40 to 128 lines of MR data per cardiac cycle.

Figure 3:
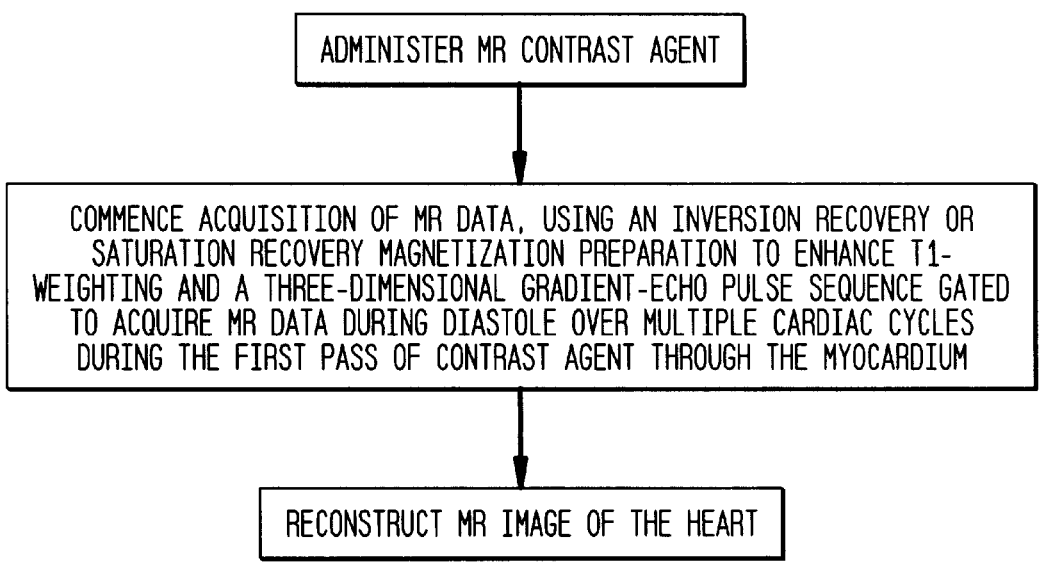
FIG. 3 is a flowchart showing a preferred embodiment of the present invention.

Hence, in accordance with a preferred embodiment of the invention as illustrated in FIG. 3, a bolus of a Gd-DTPA MR contrast agent (such as Bracco Diagnostics markets under the PROHANCE trademark) is administered to the patient (as by intravenous injection) in step 10. (The quantity of contrast agent and the details of its administration can be determined by a physician who is familiar with such matters.) Experiments have shown that the technique works best with high dose and high rate of contrast agent injection, within the recommended guidelines of the contrast agent manufacturers. When or shortly before the bolus reaches the patient's heart, data acquisition then commences (step 20). Advantageously, and in accordance with the preferred embodiment, the patient is instructed to hold his or her breath during the acquisition.

During acquisition of MR data, saturation-recovery or inversion-recovery recovery magnetization preparation is used emphasize the T1-weighting of the MR signal. As stated above, data acquisition is carried out using a T1-weighted, three-dimensional gradient echo sequence that is gated to the patient's ECG (such gating techniques are known to persons skilled in the art). Gating is carried out in such a manner that sixty-three lines of MR data are acquired in each cardiac cycle during the phase of diastole. After sixteen cardiac cycles, sufficient MR data are available to reconstruct eight sections or partitions, which can be interpolated to sixteen. Advantageously, acquisition of MR data continues until (or shortly after) the bolus of MR contrast agent passes out of the patient's heart.

Once data acquisition has been completed, the acquired lines of MR data are used (step 30) to reconstruct a T1-weighted three-dimensional image of the patient's myocardium. Bright areas in this image indicate myocardial regions that are normally perfused; dark areas indicate poorly perfused myocardial regions. The three-dimensional MR image is a static picture of the heart during diastole because the picture results from MR data that have been acquired in diastole over sixteen cardiac cycles. The dynamic properties of signal enhancement cannot be visualized from such a static image. However, the above-referenced animal experiments have shown that the reconstructed MR image has an excellent spatial resolution and signal-to-noise ratio, and accurately depicts the state of the myocardium during the first pass of contrast agent through the heart. Furthermore, signal intensity in the resultant images reflects the amount of contrast agent that perfuses the myocardium during the image acquisition (which lasts several seconds). Experiments in animals confirm that variations in signal intensity in these images correspond to differences in myocardial perfusion.

As stated above, acquisition of MR data should begin when, or shortly before, the bolus of MR contrast agent begins to make its first pass through the heart. There are a number of ways in which this result can be brought about. One way is to determine the time delay between the injection of a low-dose bolus of contrast agent and entry of the bolus into the heart, and to use this delay as a guide to postinjection commencement of MR data acquisition. Another way is to two-dimensionally image the progress of the MR contrast agent through the patient's circulatory system in real time, and to commence three-dimensional MR data acquisition when the contrast agent is detected in the left ventricle. Persons skilled in the art will be able to devise an appropriate method for synchronizing the beginning of MR data acquisition with the arrival of the bolus at the patient's heart. Although one or more preferred embodiments have been described above, the scope of the invention is defined only by the following claims:

What is claimed is:

1. A method of conducting a myocardial perfusion study on a living patient using magnetic resonance (MR) imaging, comprising the following steps:

administering a bolus of an MR contrast agent to the patient's circulatory system;

determining a time interval when the bolus makes its first pass through the patient's heart;

acquiring, during said time interval, three-dimensional MR image data of the heart, said acquiring step being gated to the patient's cardiac cycle, acquiring MR image data only during diastole, and producing MR data with high spatial resolution.

2. The method of claim 1, wherein said acquiring step is T1-weighted and uses a three-dimensional MR pulse sequence.

3. The method of claim 2, wherein the T1-weighting of the MR image data is emphasized using inversion-recovery magnetization preparation.

4. The method of claim 2, wherein the T1-weighting of the MR image data is emphasized using saturation-recovery magnetization preparation.

5. A method of carrying out a myocardial perfusion study on a living patient using magnetic resonance (MR) imaging, comprising the following steps:

administering a bolus of an MR contrast agent to the patient's circulatory system; and acquiring MR image data while the bolus is making its first pass through the patient's heart, said acquiring step being synchronized with the patient's cardiac cycle and comprising the steps of emphasizing T1-weighting of the MR signal from the myocardium, acquiring, during diastole in each of a series of cardiac cycles and using a T1-weighted three-dimensional MR pulse sequence, lines of MR data from the patient's heart, and repeating said emphasizing and line-acquiring steps until sufficient MR data has been collected to enable reconstruction of a high spatial resolution image of the heart.

6. The method of claim 5, wherein the MR pulse sequence is a gradient-echo sequence.

7. The method of claim 5, wherein the patient is instructed to hold the patient's breath during the MR image data acquisition step.

8. The method of claim 5, wherein said emphasizing step comprises the step of using magnetization preparation.

9. The method of claim 8, wherein said emphasizing step comprises the step of using inverse-recovery magnetization preparation.

10. The method of claim 8, wherein said emphasizing step comprises the step of using saturation-recovery magnetization preparation.

11. The method of claim 5, wherein said step of acquiring MR image data comprises the steps of monitoring progress of the MR contrast agent through the patient's circulatory system and beginning acquisition of MR image data when MR contrast agent enters the left ventricle of the patient's heart.

\* \* \* \* \*